United States Patent
Hirano

(10) Patent No.: US 10,327,707 B2
(45) Date of Patent: Jun. 25, 2019

(54) BIOLOGICAL INFORMATION MEASUREMENT APPARATUS AND BIOLOGICAL INFORMATION MEASUREMENT METHOD

(71) Applicant: KYOCERA Corporation, Kyoto (JP)

(72) Inventor: Asao Hirano, Koganei (JP)

(73) Assignee: KYOCERA Corporation, Kyoto (JP)

( * ) Notice: Subject to any disclaimer, the term of this patent is extended or adjusted under 35 U.S.C. 154(b) by 236 days.

(21) Appl. No.: 15/123,402

(22) PCT Filed: Mar. 17, 2015

(86) PCT No.: PCT/JP2015/001481
§ 371 (c)(1),
(2) Date: Sep. 2, 2016

(87) PCT Pub. No.: WO2015/141216
PCT Pub. Date: Sep. 24, 2015

(65) Prior Publication Data
US 2017/0065228 A1    Mar. 9, 2017

(30) Foreign Application Priority Data
Mar. 18, 2014   (JP) ................. 2014-055209

(51) Int. Cl.
*A61B 5/11* (2006.01)
*A61B 5/00* (2006.01)
*A61B 5/024* (2006.01)

(52) U.S. Cl.
CPC .......... *A61B 5/721* (2013.01); *A61B 5/02416* (2013.01); *A61B 5/6803* (2013.01); *A61B 5/6817* (2013.01); *A61B 5/11* (2013.01); *A61B 5/7221* (2013.01); *A61B 5/742* (2013.01); *A61B 2562/04* (2013.01)

(58) Field of Classification Search
CPC ... A61B 5/721; A61B 5/02416; A61B 5/6803; A61B 5/6817; A61B 5/11; A61B 5/7221; A61B 5/742; A61B 5/6814–6817; A61B 2562/04
See application file for complete search history.

(56) References Cited

U.S. PATENT DOCUMENTS 9,269,000 B2 * 2/2016 Korhonen ............. A61B 5/1118
2004/0034293 A1 2/2004 Kimball
(Continued)

FOREIGN PATENT DOCUMENTS

JP    H07-299043 A    11/1995
JP    H07-299044 A    11/1995
(Continued)

OTHER PUBLICATIONS

International Search Report issued in PCT/JP2015/001481; dated Jun. 2, 2015.
(Continued)

*Primary Examiner* — Paula J Stice
(74) *Attorney, Agent, or Firm* — Studebaker & Brackett PC

(57) ABSTRACT

A biological information measurement apparatus includes a plurality of biological sensors of the same type (111a and 111b) and a controller (120) that measures biological information based on biological measurement outputs obtained from the biological sensors (111a and 111b).

8 Claims, 6 Drawing Sheets

(56) References Cited

U.S. PATENT DOCUMENTS

| | | |
|---|---|---|
| 2008/0220535 A1 | 9/2008 | LeBoeuf et al. |
| 2010/0324615 A1 | 12/2010 | Powers |
| 2012/0022382 A1 | 1/2012 | Daisuke et al. |
| 2012/0150047 A1 | 6/2012 | Terumoto et al. |
| 2012/0203077 A1 | 8/2012 | He et al. |
| 2012/0283578 A1 | 11/2012 | LeBoeuf et al. |
| 2013/0131519 A1* | 5/2013 | LeBoeuf .............. A61B 5/0077 600/476 |

FOREIGN PATENT DOCUMENTS

| | | |
|---|---|---|
| JP | 2001-008909 A | 1/2001 |
| JP | 2006-102159 A | 4/2006 |
| JP | 2010187928 A | 9/2010 |
| JP | 2012-055593 A | 3/2012 |
| JP | 2013118904 A | 6/2013 |
| WO | 2009/036316 A1 | 3/2009 |

OTHER PUBLICATIONS

Written Opinion issued in PCT/JP2015/001481; dated Jun. 2, 2015; with English language Concise Explanation.

Extended European Search Report dated Oct. 27, 2017, from corresponding EP Appl No. 15765786.7, 8 pp.

Office Action issued by the Japanese Patent Office dated Jul. 25, 2017, which corresponds to Japanese Patent Application No. 2016-508535 and is related to U.S. Appl. No. 15/123,402; with English language statement of relevance.

* cited by examiner

Ap < A

Pn > Pa

BIOLOGICAL INFORMATION MEASUREMENT APPARATUS AND BIOLOGICAL INFORMATION MEASUREMENT METHOD

CROSS-REFERENCE TO RELATED APPLICATION

This application claims priority to and the benefit of Japanese Patent Application No. 2014-055209 filed Mar. 18, 2014, the entire contents of which are incorporated herein by reference.

TECHNICAL FIELD

This disclosure relates to a biological information measurement apparatus and a biological information measurement method.

BACKGROUND

Biological information measurement apparatuses that measure biological information of a user, such as pulse, have been proposed. Biological information is measured by a variety of methods using a biological information measurement apparatus. For example, US2008/0220535 A1 (PTL 1) and US2012/0283578 A1 (PTL 2) disclose a pulse measurement apparatus in which a compact pulse wave sensor is mounted in an earphone. By the user inserting the earphone in the ear, the pulse can be measured using the pulse wave sensor.

CITATION LIST

Patent Literature

PTL 1: US2008/0220535 A1
PTL 2: US2012/0283578 A1

SUMMARY

Technical Problem

The position of the blood vessel at the measurement site of the pulse wave, however, may shift within the user's body due, for example, to body movement by the user. Furthermore, for example when configuring an earphone as a biological information measurement apparatus, the position of the earphone might shift due to body movement or the like. In this way, if the site targeted for measurement of biological information or the position of the biological information measurement apparatus changes, noise is included in the biological information measured using the sensor, making it difficult to measure biological information accurately.

Therefore, it would be helpful to provide a biological information measurement apparatus and a biological information measurement method that can improve the measurement accuracy of biological information.

Solution to Problem

A biological information measurement apparatus according to this disclosure includes:
  a plurality of biological sensors of the same type; and
  a controller configured to measure biological information based on a plurality of biological measurement outputs obtained from the biological sensors.

The controller may calculate a biological information candidate for each of the biological measurement outputs obtained from the biological sensors, and based on a comparison of each biological information candidate, select and output one biological information candidate as a measurement result of the biological information.

The biological information measurement apparatus may further include a body movement sensor configured to detect body movement data; and
  the controller may calculate a biological information candidate for each of the biological measurement outputs obtained from the biological sensors, and based on the detected body movement data, select and output one biological information candidate as a measurement result of the biological information.

The controller may calculate a biological information candidate for each of the biological measurement outputs obtained from the biological sensors, select one biological information candidate based on a comparison of each biological information candidate, correct the selected biological information candidate using a non-selected biological information candidate, and output the corrected biological information candidate as a measurement result of the biological information.

The biological information measurement apparatus may further include a body movement sensor configured to detect body movement data; and
  the controller may calculate a biological information candidate for each of the biological measurement outputs obtained from the biological sensors, select one biological information candidate based on the detected body movement data, correct the selected biological information candidate using a non-selected biological information candidate, and output the corrected biological information candidate as a measurement result of the biological information.

The biological information measurement apparatus may further include a body movement sensor configured to detect body movement data; and
  when the detected body movement data is greater than a predetermined value, the controller may calculate a biological information candidate for each of the biological measurement outputs obtained from the biological sensors, and based on each biological information candidate, output a measurement result of the biological information; and
  when the detected body movement data is equal to or less than a predetermined value, the controller may output a measurement result of the biological information based on a biological measurement output obtained from one of the biological sensors.

The body movement sensor may detect body movement data of a site where each biological measurement output is acquired.

The biological information measurement apparatus may further include a timer configured to apply a time stamp to each biological measurement output; and
  the controller may measure the biological information based on the time stamp.

While the solution to the problem in this disclosure has been described in terms of apparatuses, this disclosure may also be implemented as methods substantially corresponding to these apparatuses, and such methods are to be understood as included in the scope of this disclosure.

For example, a method for measuring biological information according to this disclosure is a method for measuring biological information in a biological information measurement apparatus comprising a plurality of biological sensors of the same type, the method including:

measuring biological information based on a plurality of biological measurement outputs obtained from the biological sensors.

Advantageous Effect

According to the biological information measurement apparatus and biological information measurement method with the aforementioned configuration according to this disclosure, the measurement accuracy of biological information can be improved.

DETAILED DESCRIPTION

The following describes embodiments with reference to the drawings.

Figure 1:
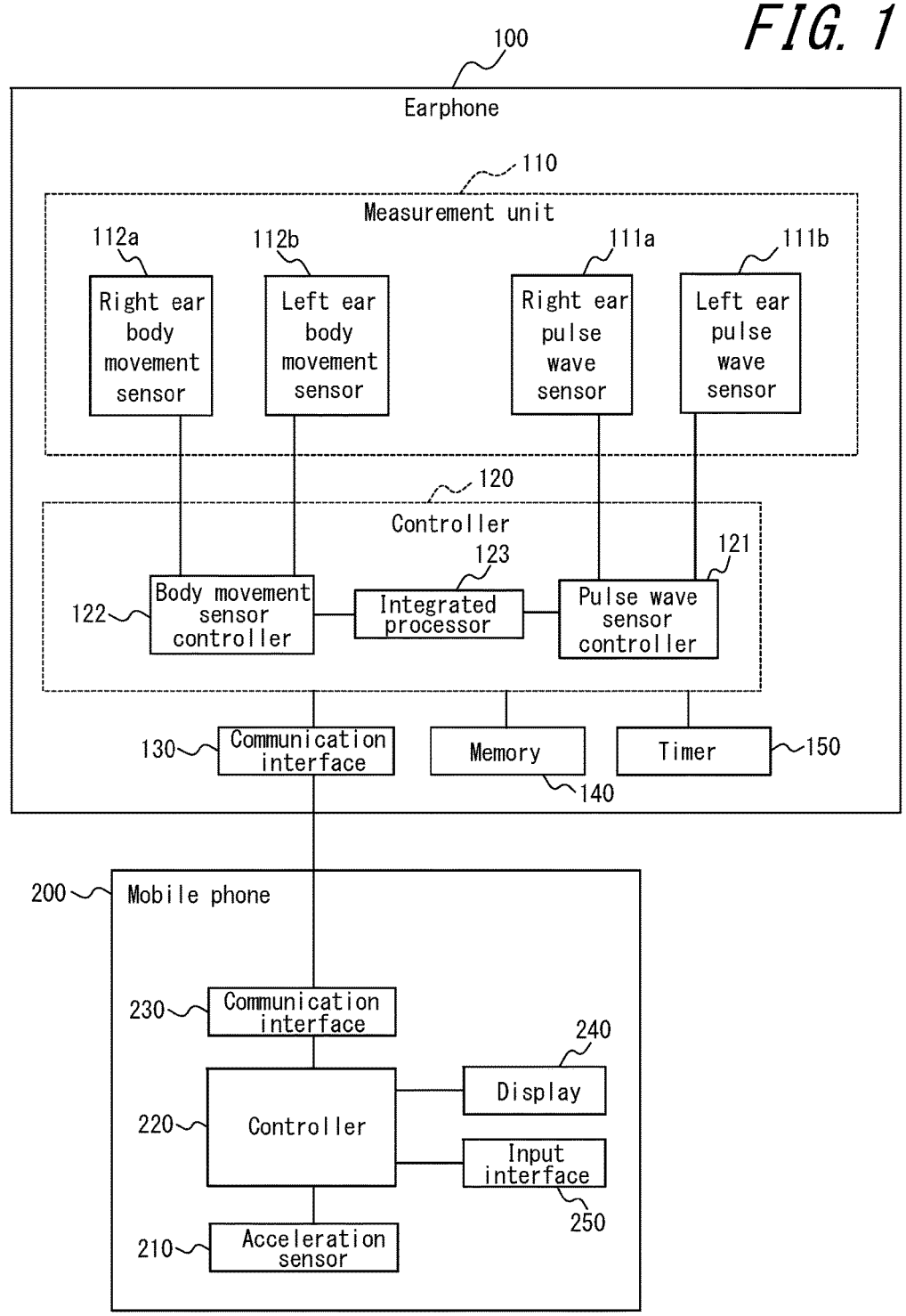
FIG. 1 is a functional block diagram of a section of the biological information measurement device according to one of the embodiments of this disclosure.

FIG. 1 is a functional block diagram of a section of the biological information measurement device according to one of the embodiments of this disclosure. The biological information measurement apparatus according to this embodiment is implemented by an earphone 100 and measures a user's pulse as biological information. The earphone 100 includes a measurement unit 110, a controller 120, a communication interface 130, a memory 140, and a timer 150. The earphone 100 that is a biological information measurement apparatus measures biological information based on biological measurement output obtained from a plurality of biological sensors of the same type, taking into consideration body movement detected by a body movement sensor and body movement data detected by an acceleration sensor 210 of a mobile phone 200 to which the earphone 100 is connected.

The measurement unit 110 includes a right ear pulse wave sensor 111a, a left ear pulse wave sensor 111b, a right ear body movement sensor 112a, and a left ear body movement sensor 112b. When not distinguishing between the right ear and the left ear, these sensors are referred to below as the pulse wave sensors 111 and the body movement sensors 112.

The pulse wave sensors 111 are each a biological sensor and acquire pulse wave data from the user (living organism) as biological measurement output. The right ear pulse wave sensor 111a is disposed in the right ear insertion portion that the user inserts in the right ear, and the left ear pulse wave sensor 111b is disposed in the left ear insertion portion that the user inserts in the left ear.

Figure 2A:
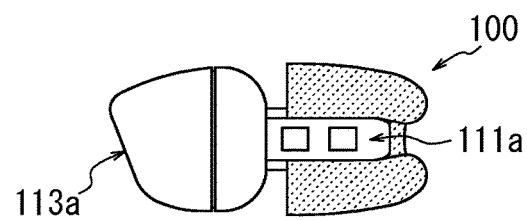
FIGS. 2A and 2B illustrate an example of the arrangement of a pulse wave sensor in an insertion portion of the earphone that is inserted in the ear.
Figure 2B:
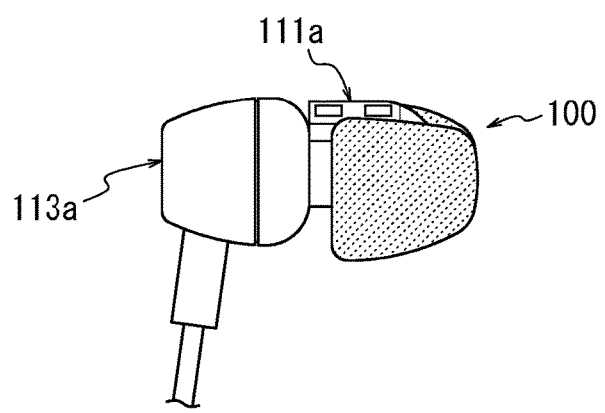
Figure 3:
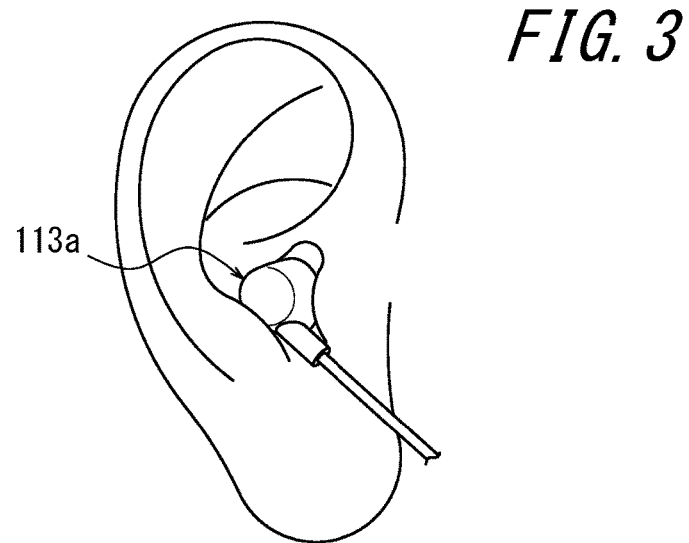
FIG. 3 illustrates the state in which the insertion portion in FIGS. 2A and 2B is inserted in the ear.

FIGS. 2A and 2B illustrate an example of the arrangement of the pulse wave sensor 111 in an insertion portion, inserted in the ear, of the earphone 100. The insertion portion illustrated in FIGS. 2A and 2B is a right ear insertion portion 113a. FIG. 2A is a top view, and FIG. 2B is a front view. The right ear pulse wave sensor 111a is, for example, provided on the upper surface of the right ear insertion portion 113a, as illustrated in FIGS. 2A and 2B. In this way, as illustrated in FIG. 3, when the user inserts the right ear insertion portion 113a in the right ear, the right ear pulse wave sensor 111a contacts the upper portion of the right ear canal and can acquire pulse wave data at the contact portion. The left ear pulse wave sensor 111b is disposed in the left ear insertion portion at a position corresponding to the above-described right ear pulse wave sensor 111a and can acquire pulse wave data on the user at the upper portion of the left ear canal. Accordingly, the right ear pulse wave sensor 111a and the left ear pulse wave sensor 111b can acquire pulse wave data at the right ear canal and the left ear canal, i.e. at different sites. The above-described arrangement of the pulse wave sensors 111 is only an example, and the pulse wave sensors 111 may for example be disposed so as to contact the lower portion or the side portion of the ear canal.

The pulse wave sensors 111 for example include a light emitting element, such as a Light Emitting Diode (LED), and a light receiving element, such as a Phototransistor (PT) or a Photodiode (PD). The pulse wave sensors 111 measure pulse wave data by irradiating a measurement location of pulse wave data in the user with light from the light emitting element and receiving reflected light with the light receiving element. In the case of such measurement with light, the pulse wave sensors 111 do not necessarily need to contact the ear canal.

The body movement sensors 112 detect body movement data of the site where biological measurement output is acquired. The body movement sensors 112 may, for example, be configured with an acceleration sensor or a gyro sensor. In this embodiment, the right ear body movement sensor 112a for example is disposed in the right ear insertion portion 113a near the right ear pulse wave sensor 111a. The left ear body movement sensor 112b for example is disposed in the left ear insertion portion near the left ear pulse wave sensor 111b. In this way, the right ear body movement sensor 112a and the left ear body movement sensor 112b detect body movement data of the site where the biological measurement output is acquired, i.e. body movement data of the upper portions of the right and left ear canals of the user. The detected body movement data is used to measure the user's biological information. Details are provided below.

The controller 120 is a processor that controls overall operations of the earphone 100. The controller 120 includes a pulse wave sensor controller 121, a body movement sensor controller 122, and an integrated processor 123 and performs various control in these functional units.

The pulse wave sensor controller 121 is connected to the pulse wave sensors 111 and monitors the pulse wave acquired by the pulse wave sensors 111 at predetermined time intervals (such as every few seconds). Based on the result of monitoring, the pulse wave sensor controller 121 calculates the pulse at predetermined time intervals. The pulse wave sensor controller 121 for example detects the peaks of the acquired pulse wave and calculates the pulse from the number of peaks. The pulse wave sensor controller 121 may detect a peak of a predetermined size or greater as a peak of the pulse wave. Based on the result of monitoring, the pulse wave sensor controller 121 determines the method of measuring the biological information. For example, the pulse wave sensor controller 121 calculates the error ratio of the pulse wave acquired by the left and right pulse wave sensors 111. The pulse wave sensor controller 121 for example judges that an error has occurred upon detecting a high pulse (for example, 220 bpm or higher) or a low pulse (for example, 30 bmp or lower) that could not normally be produced by a human body. The error rate of the pulse may, for example, be taken as the ratio of errors per unit time or the ratio of errors per calculation result. Judgment of errors is not limited to these examples. For example, the below-described abnormal waveforms may be judged to be an error.

When the error rate of the pulse wave data acquired in the left and right pulse wave sensors 111 is higher than a first threshold, the pulse wave sensor controller 121 judges that the user's body is moving and determines to measure biological information with reference to the user's body movement data detected by the below-described body movement sensors 112. Accordingly, at this time, the pulse wave sensor controller 121 transmits a command to the body movement sensor controller 122 to cause the body movement sensors 112 to operate, and the body movement sensor controller 122 that receives the command activates the body movement sensors 112. In this way, by activating the body movement sensors 112 when body movement data is necessary, the power consumption in the earphone 100 can be reduced.

When the error rate of the pulse wave data acquired in the left and right pulse wave sensors 111 is equal to or lower than a first threshold, the pulse wave sensor controller 121 determines to measure biological information based on the pulse wave data acquired from the pulse wave sensors 111. In this case, the body movement sensors 112 are not activated. Here, the pulse wave sensor controller 121 may further judge whether the error rate of the pulse wave data acquired by either of the pulse wave sensors 111 is equal to or lower than a second threshold. When the error rate of the pulse wave data acquired by either of the pulse wave sensors 111 (for one ear) is equal to or lower than the second threshold, the pulse wave sensor controller 121 determines to measure biological information based on the pulse wave data acquired from the pulse wave sensor 111 for which the error rate is equal to or lower than the second threshold. At this time, the pulse wave sensor controller 121 suspends the pulse wave sensor 111 for which the error rate is higher than the second threshold. When the error rate of the pulse wave data acquired by both pulse wave sensors 111 is higher than the second threshold, the pulse wave sensor controller 121 causes both the left and right pulse wave sensors 111 (for both ears) to operate. In this way, when the error rate of the pulse wave data acquired by one of the pulse wave sensors 111 is low, the pulse wave sensor controller 121 performs control to acquire the pulse wave data from one of the pulse wave sensors 111 and suspends the other pulse wave sensor 111, thereby reducing power consumption in the earphone 100.

The first threshold and the second threshold may, for example, be set in advance in the pulse wave sensor controller 121. The first threshold and the second threshold may, for example, also be set based on pulse wave data that the pulse wave sensor controller 121 acquired in the past. The first threshold and the second threshold may be set appropriately to different values. For example, the second threshold may be set lower than the first threshold.

The pulse wave sensor controller 121 may monitor other information related to pulse and may control operation of the pulse wave sensors 111 based on the result of monitoring. For example, the pulse wave sensor controller 121 may monitor for an abnormal waveform of the pulse wave acquired by the left and right pulse wave sensors 111 and determine the method of measuring the biological information based on the result of monitoring. The pulse wave sensor controller 121 judges that a pulse wave unobtainable from a living organism is an abnormal waveform.

Figure 4A:
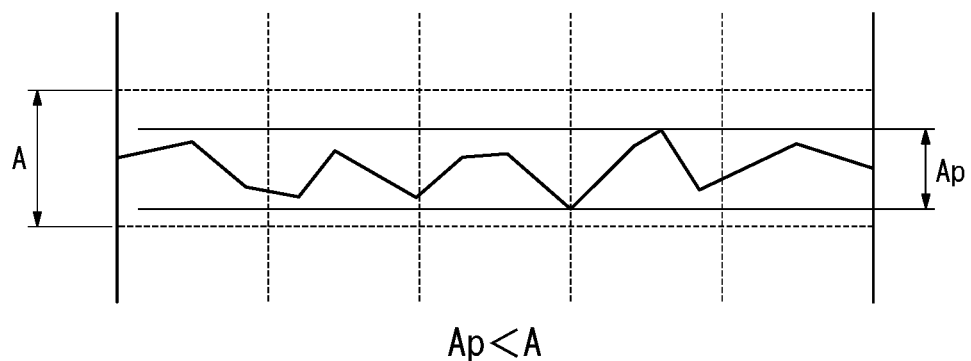
FIGS. 4A and 4B illustrate examples of abnormal waveforms acquired by the pulse wave sensor.
Figure 4B:
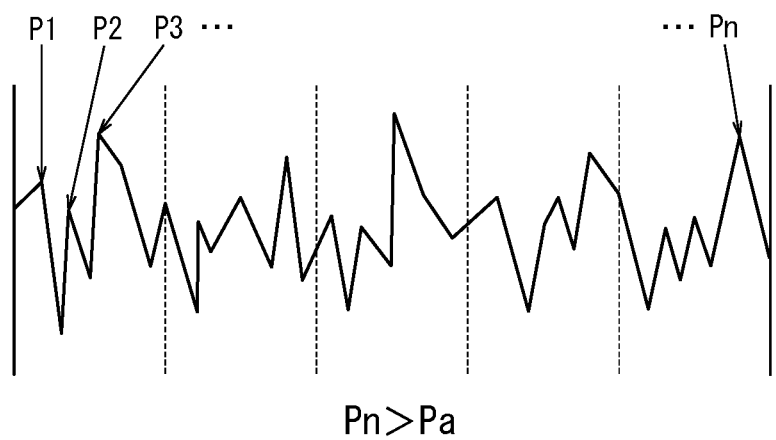

FIGS. 4A and 4B illustrate examples of abnormal waveforms. The letter A in the figures represents an appropriately set amplitude. For example, as illustrated in FIG. 4A, the pulse wave sensor controller 121 may judge that the waveform is abnormal when the difference Ap between the peak and bottom of the pulse wave within a predetermined monitoring time is smaller than the amplitude A. As another example, the pulse wave sensor controller 121 may judge that the waveform is abnormal when the number Pn of peaks in the pulse within a predetermined monitoring time is greater than a number Pa of peaks set in advance, as illustrated in FIG. 4B. The pulse wave sensor controller 121 may, for example, also judge that the waveform is abnormal when the number of peaks Pn in the pulse within a predetermined monitoring time is less than a number of peaks Pb set in advance. The numbers Pa and Pb of peaks can be set based on a high pulse and low pulse that could not normally be produced by a human body. The number Pa of peaks may, for example, be set within a range of 180 to 250 peaks/min. The number Pb of peaks may, for example, be set within a range of 20 to 40 peaks/min. The numbers Pa and Pb of peaks may, for example, be appropriately set within the aforementioned ranges based on factors such as the user's gender and age. For example, as illustrated in FIG. 4B, the pulse wave sensor controller 121 may judge that the waveform is abnormal when the height of acquired pulse peaks is not stable. The pulse wave sensor controller 121 may monitor both the error rate and the abnormal waveforms and may control operation of the pulse wave sensors 111 based on both of the results of monitoring.

When the pulse is acquired in both of the pulse wave sensors 111, the pulse wave sensor controller 121 measures the pulse, which is biological information, based on the biological measurement output acquired by the pulse wave sensors 111, i.e. the pulse wave data. Details on how the pulse wave sensor controller 121 measures the pulse are provided below.

The body movement sensor controller 122 is connected to the body movement sensors 112 and controls operations of the body movement sensors 112. The body movement sensor controller 122 also acquires the body movement data detected by the acceleration sensor 210 of the mobile phone 200 to which the earphone 100 is connected. Based on the acquired body movement data, the body movement sensor controller 122 identifies the state of body movement of the user. For example, the body movement sensor controller 122 may detect three states: a first state in which the user's head is still with respect to the body, a second state in which the user's body is still with respect to the head, and a third state that combines the first and second states. The first state for example includes both a state in which the body is not moving, such as standing up straight, and a state in which the body is moving, such as walking. The third state is, for example, a state in which the user moves the body while also performing an action such as tilting the head. In this disclosure, the portion from the user's neck upward is referred to as the head, and the portion below the neck is referred to as the body. Being still refers to the body movement data detected by the body movement sensors 112 or the acceleration sensor 210 being a predetermined threshold or less.

When the body movement data detected by the body movement sensors 112 is equal to or less than a predetermined threshold, the body movement sensor controller 122 identifies the state as being the first state. When the body movement data detected by the body movement sensors 112 is greater than a predetermined threshold and the body movement data detected by the acceleration sensor 210 is equal to or less than a predetermined threshold, the body movement sensor controller 122 identifies the state as being the second state. When the value of body movement data detected by the body movement sensors 112 is greater than a predetermined threshold and the value of body movement data detected by the acceleration sensor 210 is greater than a predetermined threshold, the body movement sensor controller 122 identifies the state as being the third state. The body movement sensor controller 122 transmits the state of body movement identified in this way to the integrated processor 123.

The integrated processor 123 processes the data used by the pulse wave sensor controller 121 and the body movement sensor controller 122. For example, based on a time stamp applied to the pulse wave data and the body movement data by the timer 150, the integrated processor 123 manages the two sets of data in association with the times at which the two sets of data were acquired. The integrated processor 123 transmits the body movement data acquired by the body movement sensor controller 122 to the pulse wave sensor controller 121. Based on the biological information measured by the pulse wave sensor controller 121, the integrated processor 123 creates display data for transmission to the mobile phone 200.

The communication interface 130 is connected to and communicates with the mobile phone 200 via a wired connection or a wireless connection such as Bluetooth® (Bluetooth is a registered trademark in Japan, other countries, or both). The display data created by the integrated processor 123 is transmitted to the mobile phone 200 from the communication interface 130. The body movement data detected by the acceleration sensor 210 of the mobile phone 200 is received from the communication interface 130.

The memory 140 may be configured with a semiconductor memory or the like. The memory 140 stores a variety of information, programs for causing the earphone 100 to operate, and the like. The memory 140 for example stores the pulse wave data acquired by the pulse wave sensors 111 and the body movement data detected by the body movement sensors 112 and the acceleration sensor 210. The memory 140 may store the pulse wave data and the body movement data in association.

The timer 150 applies a time stamp to the pulse wave data acquired by the pulse wave sensors 111, i.e. to the biological measurement output. The timer 150 also applies a time stamp to the body movement data detected by the body movement sensors 112 and the acceleration sensor 210. By applying a time stamp, the integrated processor 123 can temporally synchronize the various data.

The mobile phone 200 may, for example, be a smartphone and is connected to the earphone 100. The mobile phone 200 includes the acceleration sensor 210, a controller 220, a communication interface 230, a display 240, and an input interface 250.

The acceleration sensor 210 detects displacement of the mobile phone 200. By detecting displacement of the mobile phone 200, the acceleration sensor 210 can estimate the body movement of the user carrying the mobile phone 200. Therefore, the acceleration sensor 210 treats the detected displacement as the body movement data of the user's body.

The controller 220 is a processor that controls overall operations of the mobile phone 200. The controller 220 for example transmits the body movement data detected by the acceleration sensor 210 to the earphone 100 and displays the display data received from the earphone 100 on the display 240.

The communication interface 230 is connected to and communicates with the earphone 100 by a wired or wireless connection. The body movement data detected by the acceleration sensor 210 is transmitted to the earphone 100 from the communication interface 230. The display data created by the earphone 100 is received from the communication interface 230.

The display 240 is a display device such as a liquid crystal display, an organic EL display, an inorganic EL display, or the like. The display 240 displays the display data created by the earphone 100. The user can learn the biological information by confirming the display of the display 240.

The input interface 250 accepts operation input from the user and may be configured, for example, using operation buttons (operation keys). A portion of the display 240 may display the input interface 250 that accepts operation input from the user, and this portion may accept touch operation input by the user.

Measurement of the pulse by the pulse wave sensor controller 121 is now described. First, the case of the pulse wave sensor controller 121 referring to the user's body movement data detected by the body movement sensors 112 and determining to measure biological information is described. In this case, the pulse wave sensor controller 121 first selects one set of pulse wave data from between the sets of pulse wave data acquired by the pulse wave sensors 111 for both ears. For example, the pulse wave sensor controller 121 may select the acquired pulse wave data with the lower error rate. For example, the pulse wave sensor controller 121 may also select the acquired pulse wave data in which no abnormal waveform occurs, or the pulse wave data in which few abnormal waveforms occur. The pulse wave sensor controller 121 may, for example, also automatically select one set of pulse wave data set in advance (for example, the pulse wave data of the right ear). The pulse wave sensor controller 121 may also select the pulse wave data that, based on pulse wave data acquired in the past, tends to have less noise. As yet another example, the pulse wave sensor controller 121 may display a screen on the display 240 to prompt the user to select one of the sets of pulse wave data and then, based on user input to the input interface 250 in response to the display, select one of the sets of pulse wave data.

In accordance with the state of body movement identified by the body movement sensor controller 122, the pulse wave sensor controller 121 measures the pulse by correcting the pulse wave data using an appropriate, known correction algorithm. For example, when the body movement sensor controller 122 identifies the user's body movement as being in the first state, the pulse wave sensor controller 121 may measure the user's pulse using a preset first correction algorithm for the first state to correct the selected pulse wave data. When the user's body movement is in the second or third states as well, the pulse wave sensor controller 121 can apply a second correction algorithm or a third correction algorithm corresponding to these states. In this way, the biological information measurement apparatus measures biological information that has been appropriately corrected in accordance with the state of the user's body movement, thereby allowing improvement in the measurement accuracy of the biological information.

Next, the case of the pulse wave sensor controller 121 measuring biological information based on the pulse wave data acquired from the pulse wave sensors 111 for both ears is described. In this case, the pulse wave sensor controller 121 calculates a biological information candidate for each of a plurality of biological measurement outputs obtained from the biological sensors, and based on a comparison of the biological information candidates, selects one biological information candidate. The pulse wave sensor controller 121 can output the selected biological information candidate as the measurement result of biological information. In greater detail, first, the pulse wave sensor controller 121 calculates the pulse as a biological information candidate based on the pulse wave data acquired by each pulse wave sensor 111. The pulse wave sensor controller 121 then compares these pulses and treats one as the measurement result of the user's pulse.

Figure 5A:
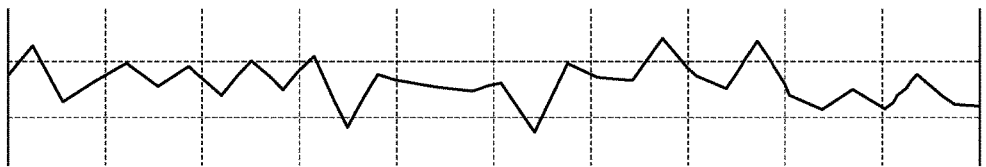
FIGS. 5A and 5B illustrate an example of pulse wave data acquired by the pulse wave sensors.
Figure 5B:
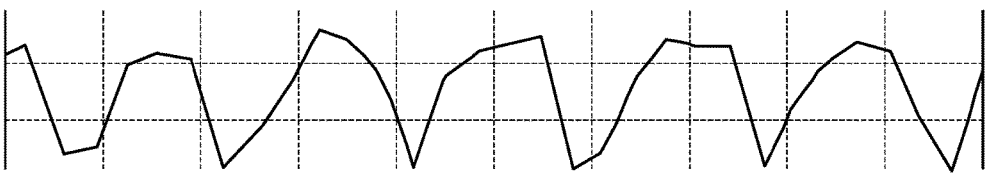

FIGS. 5A and 5B illustrate an example of pulse wave data acquired by the pulse wave sensors 111. For example, FIG. 5A is described as being the pulse wave obtained by the right ear pulse wave sensor 111a (right ear pulse wave) and FIG. 5B as being the pulse wave obtained by the left ear pulse wave sensor 111b (left ear pulse wave). Referring to FIGS. 5A and 5B, as compared to the left ear pulse wave, the right ear pulse wave has a larger number of waveform peaks, and the height of the peaks is not stable. In this case, the pulse wave sensor controller 121 judges that a larger amount of noise is included in the right ear pulse wave than in the left ear pulse wave, selects the pulse calculated based on the left ear pulse wave, and treats this pulse as the measurement result of the user's pulse. In this way, the biological information measurement apparatus can improve the measurement accuracy of the biological information.

When determining to measure the biological information based on the pulse wave data acquired from the pulse wave sensor 111 for one ear, the pulse wave sensor controller 121 calculates the pulse, which is the biological information candidate, from the pulse wave data acquired from the pulse wave sensor 111 for one ear.

Figure 6:
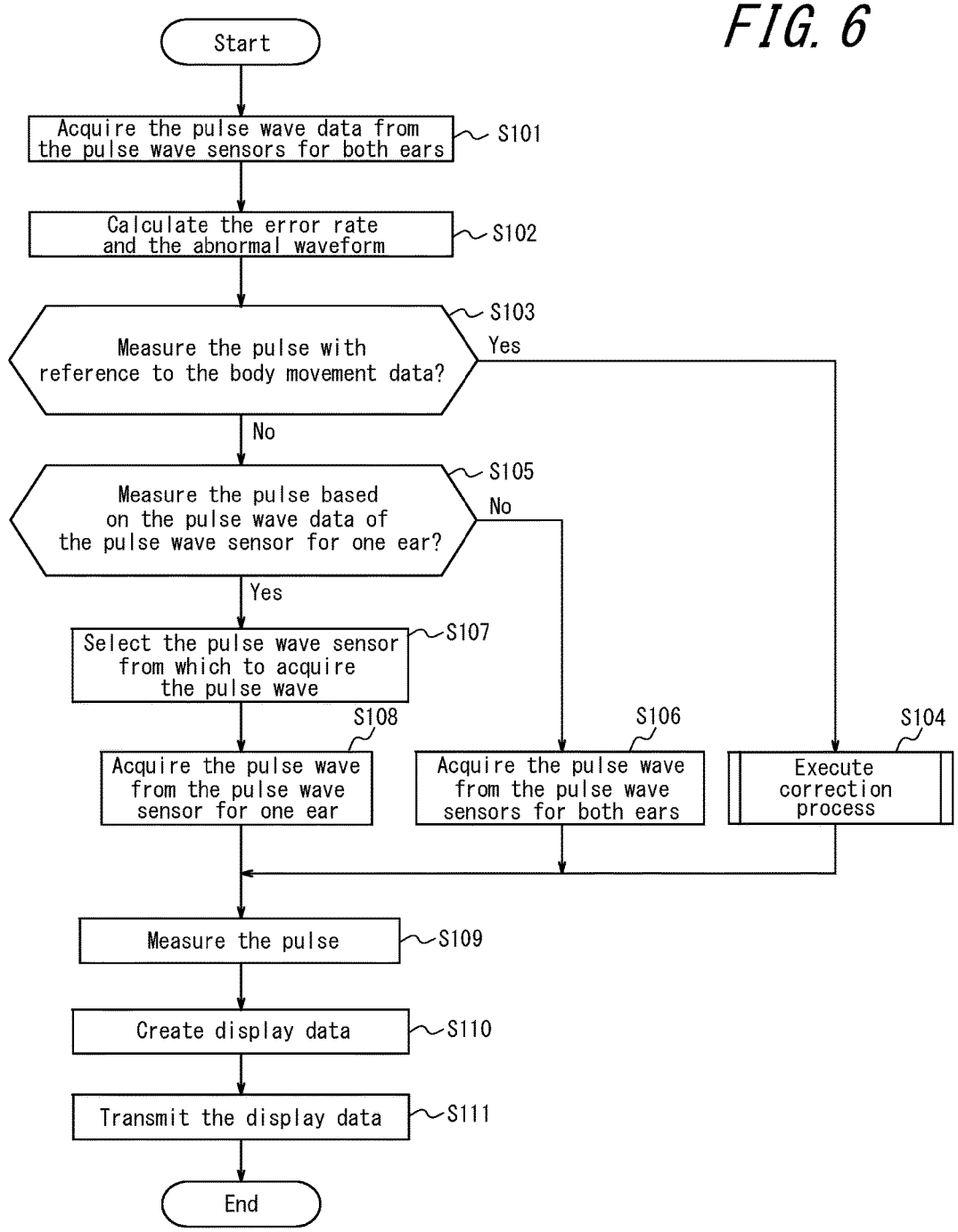
FIG. 6 is a flowchart illustrating an example of processing executed by the controller in FIG. 1.

Next, with reference to FIG. 6, an example of processing executed by the controller 120 is described. FIG. 6 is a flowchart illustrating an example of processing executed by the controller in FIG. 1. First, in the controller 120, the pulse wave sensor controller 121 acquires the pulse wave data from the pulse wave sensors 111 for both ears (step S101). The pulse wave sensor controller 121 then calculates the error rate and the abnormal waveform of the pulse wave data (step S102).

Based on the calculated error rate and abnormal waveform, the pulse wave sensor controller 121 determines the method of measuring the biological information. In greater detail, first, the pulse wave sensor controller 121 determines whether to measure the pulse with reference to the body movement data acquired by the body movement sensors 112 (step S103). For example, when the pulse wave sensor controller 121 determines to measure the pulse with reference to the body movement data because the error rate of the pulse wave data acquired in the pulse wave sensors 111 for both ears is higher than the first threshold (step S103: Yes), the controller 120 executes a correction process using a correction algorithm (step S104). Details on the correction process are provided below in the description of FIG. 7.

When the pulse wave sensor controller 121 determines not to measure the pulse with reference to the body movement data (step S103: No), then the pulse wave sensor controller 121 next determines whether to measure the pulse based on pulse wave data of the pulse wave sensor 111 for one ear (step S105). For example, when determining not to measure the pulse based on the pulse wave data of the pulse wave sensor 111 for one ear for a reason such as the error rate of the pulse wave data acquired by both pulse wave sensors 111 being higher than the second threshold (step S105: No), the pulse wave sensor controller 121 acquires the pulse wave from the pulse wave sensors 111 for both ears (step S106).

When determining to measure the pulse based on the pulse wave data of the pulse wave sensor 111 for one ear (step S105: Yes), then based on the error rate or the like of the pulse data, the pulse wave sensor controller 121 selects one of the pulse wave sensors 111 from which to acquire the pulse wave (step S107). The pulse wave sensor controller 121 then acquires the pulse wave from the selected pulse wave sensor 111 (step S108).

Based on the waveform acquired in step S104, step S106, or step S107, the pulse wave sensor controller 121 then measures the pulse (step S109). Subsequently, the integrated processor 123 creates display data from the measured pulse (step S110). The controller 120 then transmits the display data to the mobile phone 200 via the communication interface 130 (step S111). The display data transmitted in this way is displayed on the display 240, so that the user can learn the pulse by confirming the display of the display 240.

Figure 7:
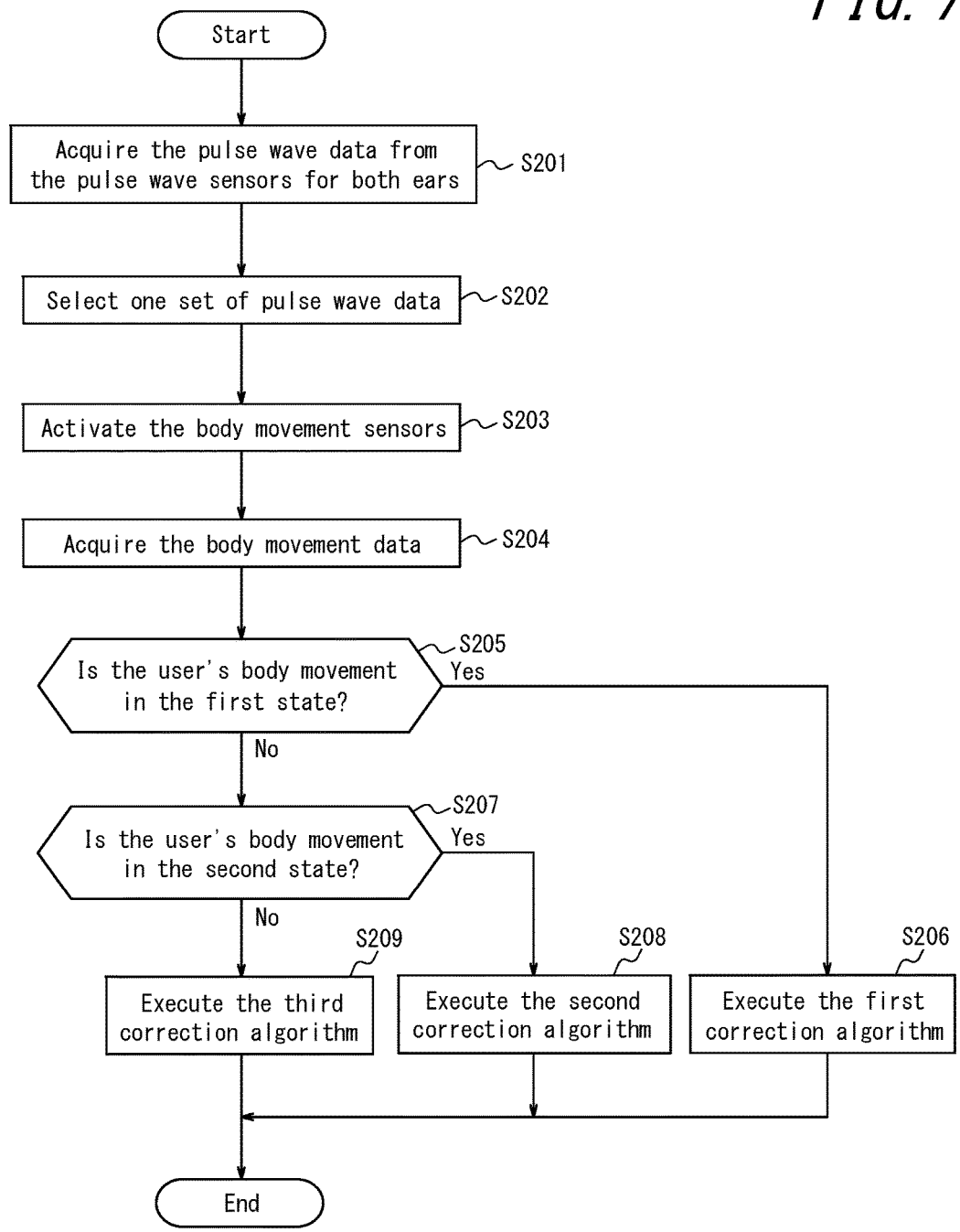
FIG. 7 is a flowchart illustrating an example of processing executed by the controller in FIG. 1.

Next, the correction process of step S104 is described with reference to FIG. 7. FIG. 7 is a flowchart illustrating an example of processing executed by the controller 120 in FIG. 1. This flowchart illustrates an example of the processing in step S104 in detail. When the pulse wave sensor controller 121 determines to measure the pulse with reference to the body movement data (step S103: Yes), the pulse wave sensor controller 121 acquires the pulse wave from the pulse wave sensors 111 for both ears (step S201). Between the sets of pulse wave data, the pulse wave sensor controller 121 then selects the set of pulse wave data that has less noise (step S202).

Next, the body movement sensor controller 122 activates the body movement sensors 112 (step S203). The body movement sensor controller 122 acquires the user's body movement data detected by the body movement sensors 112 (step S204).

The body movement sensor controller 122 then judges whether the user's body movement is in the first state (step S205). When the body movement sensor controller 122 judges that the user's body movement is in the first state (step S205: Yes), the pulse wave sensor controller 121 executes the first correction algorithm on the pulse wave data selected in step S202 (step S206). Since the first state is, for example, a state in which the body is moving, such as walking, the pulse wave sensor controller 121 may, for example, execute a known walking/running correction algorithm as the first correction algorithm.

When judging that the user's body movement is not in the first state (step S205: No), the body movement sensor controller 122 then judges whether the user's body movement is in the second state (step S207). When the body movement sensor controller 122 judges that the user's body movement is in the second state (step S207: Yes), the pulse wave sensor controller 121 executes the second correction algorithm on the pulse wave data selected in step S202 (step S208). Since the second state is, for example, a state in which the head is moving while the body is still, the pulse wave sensor controller 121 may, for example, execute a known head correction algorithm as the second correction algorithm.

When judging that the user's body movement is not in the second state (step S207: No), the body movement sensor controller 122 judges that the user's body movement is in the third state, and the pulse wave sensor controller 121 executes the third correction algorithm on the pulse wave data selected in step S202 (step S209). Since the third state is, for example, a state in which the user moves the body while also performing an action such as tilting the head, the pulse wave sensor controller 121 may, for example, execute a known whole body movement correction algorithm as the third correction algorithm.

Upon completion of the correction algorithm by the pulse wave sensor controller 121, the correction process terminates. In step S109 of FIG. 6, as described above, the pulse wave sensor controller 121 measures the pulse, the integrated processor 123 creates display data (step S110), and the display data is transmitted to the mobile phone 200 (step S111).

By the earphone 100, which is a biological information measurement apparatus, thus acquiring pulse wave data from a plurality of pulse wave sensors 111, the earphone 100 can measure the pulse using a method with a higher measurement accuracy in accordance with the sets of pulse wave data. By using the body movement sensors 112, the earphone 100 can also measure the pulse by taking into consideration the effect of noise due to body movement. Therefore, with the earphone 100, the measurement accuracy of biological information improves.

The present disclosure is not limited to the above embodiment, and a variety of modifications and changes are possible. For example, the functions and the like included in the various components and steps may be reordered in any logically consistent way. Furthermore, components or steps may be combined into one or divided.

For example, in FIG. 1, the controller 120 is provided in the earphone 100, but the controller 120 may be provided in another, independent apparatus instead. In other words, the measurement unit 110 and the controller 120 may be configured as separate devices that are connected so as to be able to communicate with each other over a wired or wireless connection.

In the above embodiment, the body movement sensors 112 have been described as being disposed near the left and right pulse wave sensors 111 in the left and right insertion portions, but the number and position of the body movement sensors 112 is not limited to this example. As appropriate, the necessary number of body movement sensors 112 for detecting body movement at the sites at which the pulse wave sensors 111 acquire biological measurement output may be disposed. For example, in the case of a headphone in which the relative positions of the left and right insertion portions do not change due to the two insertion portions being physically connected by a connecting portion that extends across the back or top of the head, one body movement sensor 112 may be disposed at the center of the connecting portion.

The method of measuring biological information, for example, is not limited to the method indicated in the above embodiment. For example, the pulse wave sensor controller 121 may calculate a biological information candidate for each of a plurality of biological measurement outputs obtained from the plurality of biological sensors, and based on the detected body movement data, may output one of the biological information candidates as the measurement result of biological information. In greater detail, first, the pulse wave sensor controller 121 calculates the pulse as a biological information candidate based on the pulse wave data acquired by each pulse wave sensor 111. Via the integrated processor 123, the pulse wave sensor controller 121 then acquires the body movement data detected by the body movement sensors 112, and based on the body movement data, treats a pulse detected with high accuracy among the calculated pulses as the measurement result.

For example, suppose that by the user tilting the neck to the left while keeping the body still, the position of the left ear lowers, and the position of the right ear rises. The body movement sensor 112 detects such movement by the user, and via the integrated processor 123, the body movement sensor controller 122 transmits the detected body movement data to the pulse wave sensor controller 121. When the user tilts the neck to the left, the left ear insertion portion tends to shift position due to gravity, making it easy for more noise to be included in the left ear pulse wave than in the right ear pulse wave. Therefore, based on the received body movement data, the pulse wave sensor controller 121 judges that more noise is included in the left ear pulse wave than in the right ear pulse wave. The pulse wave sensor controller 121 then treats the pulse calculated based on the right ear pulse wave as the measurement result of the user's pulse. In this way, the biological information measurement apparatus can improve the measurement accuracy of the biological information.

As another example, the pulse wave sensor controller 121 may calculate a biological information candidate for each of a plurality of biological measurement outputs obtained from the biological sensors, and based on a comparison of the biological information candidates, may select one biological information candidate. At this time, the pulse wave sensor controller 121 may correct the selected biological information candidate using the non-selected biological information candidates and output the corrected biological information candidate as the measurement result of biological information. For example, suppose that the pulse wave sensor controller 121 calculates the pulse from each of the measured pulse waves for both ears and selects the pulse calculated based on the left ear pulse wave as the biological information candidate. Here, suppose for example that the error rate of the pulse wave during a predetermined time period for the acquired left ear pulse wave is temporarily lower than the error rate of the pulse wave during a corresponding time period for the right ear pulse wave. In this case, the pulse wave sensor controller 121 can make corrections during this time period so as to measure the user's pulse based on the right ear pulse wave rather than the left ear pulse wave. In this way, the measurement accuracy of the biological information is further improved.

As another example, the pulse wave sensor controller 121 may calculate a biological information candidate for each of a plurality of biological measurement outputs obtained from the biological sensors, and based on the detected body movement data, may select one biological information candidate. At this time, the pulse wave sensor controller 121 may correct the selected biological information candidate using the non-selected biological information candidates and output the corrected biological information candidate as the measurement result of biological information. For example, suppose that the pulse wave sensor controller 121 calculates the pulse from each of the measured pulse waves for both ears and selects the pulse calculated based on the left ear pulse wave as the biological information candidate. Furthermore, via the integrated processor 123, the pulse wave sensor controller 121 receives the body movement data detected by the body movement sensors 112. Here, suppose that the user tilts the neck to the left for a few seconds and that the body movement sensors 112 detect this movement. At this time, with regard to the information on the pulse for the few seconds during which the user tilts the neck, the pulse wave sensor controller 121 can correct the information on the selected left ear pulse wave using the information on the right ear pulse wave. In greater detail, for example for the few seconds during which the user tilts the head, the pulse wave sensor controller 121 can make corrections so as to measure the user's pulse based on the right ear pulse wave rather than the left ear pulse wave. In this way, the measurement accuracy of the biological information is further improved.

For example, the pulse wave sensor controller 121 can vary the method of measuring biological information in accordance with the body movement data detected by the body movement sensors 112. When, for example, the body movement data detected by the body movement sensors 112 and the acceleration sensor 210 is larger than a predetermined value, the pulse wave sensor controller 121 may calculate a biological information candidate for each of a plurality of biological measurement outputs obtained from the biological sensors. Based on the biological information candidates, the pulse wave sensor controller 121 then outputs the measurement result of biological information. On the other hand, when the body movement data detected by the body movement sensors 112 and the acceleration sensor 210 is equal to or less than a predetermined value, the pulse wave sensor controller 121 can output the measurement result of biological information based on the biological measurement output from one of the biological sensors.

In greater detail, a predetermined value of body movement data serving as a standard for determining the method of measuring the pulse is stored in advance in the body movement sensor controller 122, and the body movement sensor controller 122 first judges whether the body movement data detected by the body movement sensor 112 and the acceleration sensor 210 is greater than the predetermined value. When the value of the body movement data is greater than the predetermined value, the user's body movement is large, and there is a high probability of a large amount of noise being included in the pulse wave data acquired by the pulse wave sensor 111. For each set of pulse wave data acquired by the pulse wave sensors 111 for both ears, the pulse wave sensor controller 121 calculates the pulse as a biological information candidate, and based on the calculated pulse, outputs the measurement result of the user's pulse. The measurement result of the user's pulse may be output in a variety of ways. For example, at each predetermined time interval, the pulse may be selected based on the pulse wave data that has little noise and may be output as the measurement result of the user's pulse. The judgment of whether much noise is included may, for example, be made with reference to the body movement data detected by the body movement sensors 112 and the acceleration sensor 210.

On the other hand, when the value of the body movement data is equal to or less than a predetermined value, the user is in a state of little body movement, such as a still state. Therefore, it is assumed that even with only one of the left and right pulse wave sensors 111, highly accurate biological information can be acquired. In this case, the pulse wave sensor controller 121 selects one of the pulse wave sensors 111 and outputs the measurement result of the user's pulse based on the pulse wave data acquired by the selected pulse wave sensor 111. The selection of one of the pulse wave sensors 111 may, for example, be made by selecting the pulse wave sensor 111 that tends to have little noise based on data acquired in the past, or by selection through user input to the input interface 250. In this way, the measurement result of the pulse is output based on pulse data of a plurality of pulse wave sensors 111 when the user's body movement is large, whereas only one pulse wave sensor 111 is caused to operate when the user's body movement is slight. Hence, the earphone 100 can reduce power consumption while improving the detection accuracy of biological information.

In this way, the earphone 100 that is a biological information detection apparatus can measure biological information by a variety of methods. Several methods of measuring biological information have been described so far, but the method of measuring biological information is not limited to the above-described methods. Any other method may also be used. A plurality of methods may also be used together to measure biological information. Furthermore, the plurality of biological sensors of the same type may use different methods of measurement, as long as the biological sensors can measure the same type of biological information. For example, when using pulse sensors as the biological sensors, pulse sensors with a variety of methods of measurement may be used, such as a sensor with a method of measurement using light, a sensor with a method of measurement using a camera, a sensor with a method of measurement using electrodes, and the like.

In the above embodiment, the biological information measurement apparatus has been described as being the earphone 100, but the biological information measurement apparatus is not limited to being the earphone 100 and may be configured using any item that the user wears or carries. For example, the biological information measurement apparatus can be configured using eyeglasses. In this case, the eyeglasses can acquire pulse wave data by mounting a pulse wave sensor at a location in the eyeglass frame that contacts the user's temple. Other examples include configuring a ring or other accessory, wristband, wristwatch, hat, sock, supporter worn on the elbow or the knee, or other such item as the biological information measurement apparatus.

Furthermore, the biological information measurement apparatus may be configured using a plurality of types of items. For example, the biological information measurement apparatus may be configured using an earphone and a wristband and may measure the user's pulse by acquiring pulse wave data from a pulse wave sensor provided in each of the earphone and the wristband. The plurality of types of items may be combined freely. In the biological information measurement apparatus configured using such a plurality of types of items, the items are connected to each other by a wired or wireless connection.

In this way, by configuring the biological information measurement apparatus using different items, pulse wave data can be acquired at different sites on the user's body. In accordance with the time of day, the user's state of body movement, or the like, the measurement accuracy of the pulse wave data may change by site. Therefore, by thus acquiring the pulse wave data at different sites, it is expected that the measurement accuracy of biological information can be further improved.

Furthermore, when the biological information measurement apparatus is configured using a plurality of types of items in this way, the timer 150 can apply a time stamp to the pulse wave data acquired from the pulse wave sensor provided in each item. Based on the time stamp, for example biological information such as the rate of blood flow can be measured to a high degree of accuracy from the pulse wave data acquired by different items at different locations.

In the above embodiment, the method of measuring a pulse as biological information has been described, but the biological information is not limited to pulse. The biological information may, for example, be any other information related to the user's body, such as the user's body temperature, the blood oxygen level, or the like. For example, the biological information measurement apparatus can acquire the pulse wave data as in the above embodiment, and by detecting a change in the interval between peaks of the pulse wave, determine the state of the autonomic nervous system.

In the above embodiment, the biological information measurement apparatus is connected to the mobile phone 200, and the user's body movement is detected by the acceleration sensor 210 of the mobile phone 200, but detection of the user's body movement is not limited to the mobile phone 200. For example, any electronic device can detect the user's body movement, such as a portable music player. The user's body movement can also be detected using a dedicated device for the biological information detection apparatus instead of the mobile phone 200.

REFERENCE SIGNS LIST

100 Earphone
110 Measurement unit
111 Pulse wave sensor
111a Right ear pulse wave sensor
111b Left ear pulse wave sensor
112 Body movement sensor
112a Right ear body movement sensor
112b Left ear body movement sensor
120 Controller
121 Pulse wave sensor controller
122 Body movement sensor controller
123 Integrated processor
130 Communication interface
140 Memory
150 Timer
200 Mobile phone
210 Acceleration sensor
220 Controller
230 Communication interface
240 Display
250 Input interface

The invention claimed is:

1. A biological information measurement apparatus comprising:
a right earphone and a left earphone, each earphone comprising:
a body movement sensor configured to measure body movement, and a pulse wave sensor configured to measure pulse waves;
a controller comprising:
a body movement sensor controller configured to monitor body movement signals based on the measured body movements obtained from the body movement sensors,
a pulse wave controller configured to monitor pulse wave signals based on the measured pulse waves obtained from the pulse wave sensors, and
an integrated processor;
a communications interface; and
a memory,
wherein the body movement sensor is selected from the group consisting of at least one of an acceleration sensor and a gyro sensor.

2. The biological information measurement apparatus of claim 1,
wherein
the controller is configured to calculate a body movement signal candidate for each of the body movement signals obtained from the body movement sensors, and based on the measured body movement data, output one body movement signal candidate as a measurement result of the body movement signal.

3. The biological information measurement apparatus of claim 2, wherein the body movement sensor is configured to measure body movement data of a site where each body movement signal is acquired.

4. The biological information measurement apparatus of claim 1, wherein the controller is configured to calculate a body movement signal candidate for each of the body movement signals obtained from the body movement sensors, select one body movement signal candidate based on a comparison of each body movement signal candidate, correct the selected body movement signal candidate using a non-selected body movement signal candidate, and output the corrected body movement signal candidate as a measurement result of the body movement signal.

5. The biological information measurement apparatus of claim 1,
wherein
the controller is configured to calculate a body movement signal candidate for each of the body movement signals obtained from the body movement sensors, select one body movement signal candidate based on the measured body movement data, correct the selected body movement signal candidate using a non-selected body movement signal candidate, and output the corrected body movement signal candidate as a measurement result of the body movement signal.

6. The biological information measurement apparatus of claim 1,
wherein
when the measured body movement data is greater than a predetermined value, the controller is configured to calculate a body movement signal candidate for each of the body movement signals obtained from the body movement sensors, and based on each body movement signal candidate, output a measurement result of the body movement signal; and
when the measured body movement data is equal to or less than a predetermined value, the controller is configured to output a measurement result of the body movement signal based on a body movement signal obtained from one of the body movement sensors.

7. The biological information measurement apparatus of claim 1, further comprising:
a timer configured to apply a time stamp to each body movement signal; wherein
the controller is configured to monitor the body movement signal based on the time stamp.

8. A method for measuring body movement information and pulse wave information in a right earphone and a left earphone, each earphone comprising a body movement sensor and a pulse wave sensor, the method comprising:
acquiring a body movement signal from each of the body movement sensors,
acquiring a pulse wave signal from each of the pulse wave sensors, calculating error rate of the pulse wave signals,
measuring pulse with reference to the body movement signals if the error rate in both earphones is greater than a predetermined threshold,
measuring the pulse based on pulse wave data of the sensor for one of the right or left earphone if the error rate in the one earphone is equal to or less than the predetermined threshold,
selecting the appropriate pulse sensor from which to acquire the pulse wave data, and
displaying and transmitting the data.

\* \* \* \* \*